United States Patent [19]
Julian et al.

[11] Patent Number: 5,968,904
[45] Date of Patent: Oct. 19, 1999

[54] MODIFIED ARGININE CONTAINING LYTIC PEPTIDES AND METHOD OF MAKING THE SAME BY GLYOXYLATION

[75] Inventors: Gordon R. Julian, Bozeman, Mont.; Jesse M. Jaynes, Raleigh, N.C.

[73] Assignee: Demegen, Inc., Pittsburgh, Pa.

[21] Appl. No.: 08/475,328

[22] Filed: Jun. 7, 1995

Related U.S. Application Data

[63] Continuation-in-part of application No. 08/231,730, Apr. 20, 1994, Pat. No. 5,561,107, which is a continuation-in-part of application No. 08/225,476, Apr. 8, 1994, abandoned, which is a continuation-in-part of application No. 08/039,620, Jun. 4, 1993, abandoned, application No. 08/148,889, Nov. 8, 1993, abandoned, and application No. 08/148,491, Nov. 8, 1993, abandoned.

[51] Int. Cl.$^6$ .......................... A61K 38/10; A61K 38/16; C07K 7/08; C07K 14/00
[52] U.S. Cl. ............................. 514/12; 514/13; 530/324; 530/325; 930/10; 930/20
[58] Field of Search ........................ 514/12, 13; 530/324, 530/325

[56] References Cited

U.S. PATENT DOCUMENTS

| | | | |
|---|---|---|---|
| 4,355,104 | 10/1982 | Hultmark et al. | 435/70 |
| 4,520,016 | 5/1985 | Hultmark et al. | 514/12 |
| 4,810,777 | 3/1989 | Zasloff | 530/326 |
| 5,045,531 | 9/1991 | Berkowitz et al. | 514/12 |
| 5,070,188 | 12/1991 | Njieha et al. | 530/324 |
| 5,242,902 | 9/1993 | Murphy et al. | 514/12 |
| 5,294,605 | 3/1994 | Houghton et al. | 514/13 |
| 5,411,942 | 5/1995 | Widmer et al. | 514/17 |
| 5,424,290 | 6/1995 | Maloy et al. | 514/13 |
| 5,561,107 | 10/1996 | Jaynes et al. | 514/12 |

FOREIGN PATENT DOCUMENTS

| | | |
|---|---|---|
| 0365598 | 1/1989 | European Pat. Off. |
| 0383770 | 1/1989 | European Pat. Off. |
| 9012866 | 11/1990 | WIPO |

OTHER PUBLICATIONS

Takahashi, K. J. Biochem. (Tokyo), 81(2), 403–14, Feb. 1977.

Arrowood M. et al. Antimicrob. Agents Chemother., 35(2), 224–7, Feb. 1991.

Habeeb, A.S.F.A., "Determination of Free Amino Groups in Proteins . . . Acid", Anal. Biochem., 14:328–336 (1966).

Liu et al., "Modification of Arginines in Trypsin . . . Cyclohexanedione", Biochem. 7(8) 2886–92 (1968).

Jaynes et al., "In Vitro Cytocidal Effect of Lytic Peptides . . . Cell Lines" Peptide Research, 2:157–160 (1989).

Jaynes, "Lytic Peptides Portend an Innovative Age in the Management . . . Human Disease", Drug News & Perspective, 3:69–78 (1990).

Reed et al., "Enhanced in Vitro Growth of Murine Fibroblast Cells . . . Peptide", Molecular Reproduction & Development, 31:106–113 (1992).

Akerfeldt et al., "Synthetic Peptides as Models for Ion Channel Proteins", Acc. Chem. Res., 26:191–197 (1993).

Arrowood et al., "Hemolytic Properties of Lytic Peptides Active . . . *Cryptosporidium Parvum*", J. Protozool., 38:161S–163S (1991).

Jaynes et al., "In vitro cytocidal effect of novel lytic peptides on . . . *Trypanosoma cruzi*", Faseb J., 2:2878–2883 (1988).

Graham et al., "Cytoxic Effect of Amphipathic Cationic Lytic Peptides on . . . Lines", Proc. of Amer. Assoc. for Cancer Res., 35:410 (1994).

Moore et al., "Preliminary Experimental Anti–Cancer . . . Cecropin β", Proc. of Amer. Assoc. for Cancer Res., 35:410 (1994).

Means et al., "Reductive Alkylation of Amino Groups in Proteins", Biochem., 7:2192–2201 (1968).

Takahashi, "The Reaction of Phenylglyoxal with Arginine . . . ", J. Biol. Chem., 243:6171–6179 (1968).

Yankeelov et al., "Methylmaleic Anhydride as a Reversible . . . Modification", Biochem. & Biophysical Research Comm. 42(5):886–891 (1971).

Busby et al., "Chemical Modifications of Lysyl & Arginyl . . . Antitrypsin", Archives of Biochem. & Biophys., 177:552–560 (1976).

Lin et al., "Chemical Modification of Arginine . . . α–Bungarotoxin", Biochem. et Biophys. Acta., 1159:255–261 (1992).

Patthy et al., "Identification of Functional Arginine . . . Lysozyme", J. Biol. Chem. 250(2) 565–569 (1975).

Gorecki et al., "Non Cationic Substrates of Trypsin", Biochem. & Biophys. Res. Comm., 29(2):189–193 (1967).

*Primary Examiner*—Cecilia J. Tsang
*Assistant Examiner*—Michael Borin
*Attorney, Agent, or Firm*—Rothwell, Figg, Ernst & Kurz

[57] ABSTRACT

A non-neurotoxin, arginine residue-containing non-naturally occurring lytic peptide comprising a sequence of amino acid residues in sufficient number and arrangement to confer lytic activity to the peptide, wherein the guanido groups of the arginine residues and the α-amino group of the N-terminal amino acid are sufficiently glyoxylated to impart enhanced tryptic, chymotryptic, and aminopeptidase digestion resistance to the peptide. The compositions of the invention are suitable for in vivo administration. A method of-making the same, to impart enhanced tryptic digestion resistance thereto, comprising glyoxylating the guanido groups of the arginine residues and the α-- amino group of the N-terminal amino acid with glyoxa containing buffer for sufficient time and at sufficient conditions to glyoxylate the side chain and α-amino groups to sufficient extent to confer enhanced proteolytic digestion resistance to the peptide.

10 Claims, No Drawings

SEQUENCE LISTING (1) GENERAL INFORMATION:

(iii) NUMBER OF SEQUENCES: 8

(2) INFORMATION FOR SEQ ID NO: 7:

(i) SEQUENCE CHARACTERISTICS:
         (A) LENGTH: 27
         (B) TYPE: AMINO ACID
         (C) TOPOLOGY: LINEAR (ii) MOLECULE TYPE:
         (A) DESCRIPTION: PEPTIDE (iii) HYPOTHETICAL: NO (v) FRAGMENT TYPE: COMPLETE PEPTIDE (xi) SEQUENCE DESCRIPTION: SEQ ID NO: 7:

Phe Ala Val Gly Leu Arg Ala Ile Lys Arg Ala Leu Lys Lys Leu Arg
 1               5                  10                  15

Arg Gly Val Arg Lys Val Ala Lys Arg Lys Arg
            20                  25

(2) INFORMATION FOR SEQ ID NO: 8:

(i) SEQUENCE CHARACTERISTICS:
         (A) LENGTH: 23
         (B) TYPE: AMINO ACID
         (C) TOPOLOGY: LINEAR (ii) MOLECULE TYPE:
         (A) DESCRIPTION: PEPTIDE (iii) HYPOTHETICAL: NO (v) FRAGMENT TYPE: COMPLETE PEPTIDE (xi) SEQUENCE DESCRIPTION: SEQ ID NO: 8:

Phe Ala Val Gly Leu Arg Ala Ile Lys Arg Ala Leu Lys Lys Leu Arg
 1               5                  10                  15

Arg Gly Val Arg Lys Val Ala
            20

(2) INFORMATION FOR SEQ ID NO: 9:

(i) SEQUENCE CHARACTERISTICS:
         (A) LENGTH: 27
         (B) TYPE: AMINO ACID
         (C) TOPOLOGY: LINEAR (ii) MOLECULE TYPE:
         (A) DESCRIPTION: PEPTIDE (iii) HYPOTHETICAL: NO (v) FRAGMENT TYPE: COMPLETE PEPTIDE (xi) SEQUENCE DESCRIPTION: SEQ ID NO: 9:

Lys Arg Lys Arg Ala Val Lys Arg Val Gly Arg Arg Leu Lys Lys Leu
 1               5                  10                  15

Ala Arg Lys Ile Ala Arg Leu Gly Val Ala Phe
            20                  25

(2) INFORMATION FOR SEQ ID NO: 10:

(i) SEQUENCE CHARACTERISTICS:

(A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (xi) SEQUENCE DESCRIPTION: SEQ ID NO: 10:

Ala Val Lys Arg Val Gly Arg Arg Leu Lys Lys Leu Ala Arg Lys Ile
1               5                   10                  15

Ala Arg Leu Gly Val Ala Phe
            20

(2) INFORMATION FOR SEQ ID NO: 11:

(i) SEQUENCE CHARACTERISTICS:
        (A) LENGTH: 30
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (xi) SEQUENCE DESCRIPTION: SEQ ID NO: 11:

Phe Ala Val Gly Leu Arg Ala Ile Lys Arg Ala Leu Lys Lys Leu Arg
1               5                   10                  15

Arg Gly Val Arg Lys Val Ala Lys Arg Lys Arg Lys Lys Asp
            20                  25                  30

(2) INFORMATION FOR SEQ ID NO: 12:

(i) SEQUENCE CHARACTERISTICS:
        (A) LENGTH: 26
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (xi) SEQUENCE DESCRIPTION: SEQ ID NO: 12:

Phe Ala Val Gly Leu Arg Ala Ile Lys Arg Ala Leu Lys Lys Leu Arg
1               5                   10                  15

Arg Gly Val Arg Lys Val Ala Lys Asp Leu
            20                  25

(2) INFORMATION FOR SEQ ID NO: 13:

(i) SEQUENCE CHARACTERISTICS:
        (A) LENGTH: 30
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (xi) SEQUENCE DESCRIPTION: SEQ ID NO: 13:

```
Lys Arg Lys Arg Ala Val Lys Arg Val Gly Arg Arg Leu Lys Lys Leu
1               5                   10                  15

Ala Arg Lys Ile Ala Arg Leu Gly Val Ala Phe Lys Asp Leu
            20                  25                  30
```

(2) INFORMATION FOR SEQ ID NO: 14:

(i) SEQUENCE CHARACTERISTICS:
        (A) LENGTH: 26
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (xi) SEQUENCE DESCRIPTION: SEQ ID NO: 14:

```
Ala Val Lys Arg Val Gly Arg Arg Leu Lys Lys Leu Ala Arg Lys Ile
1               5                   10                  15

Ala Arg Leu Gly Val Ala Phe Lys Asp Leu
            20                  25
```

MODIFIED ARGININE CONTAINING LYTIC PEPTIDES AND METHOD OF MAKING THE SAME BY GLYOXYLATION

This is a continuation-in-part of Ser. No. 08/231,730, filed Apr. 20, 1994, now U.S. Pat. No. 5,561,107, which is a continuation-in-part of Ser. No. 08/225,476, filed Apr. 8, 1994, abandoned, which is a continuation-in-part of Ser. No. 08/039,620, filed Jun. 4, 1993, abandoned, and a continuation-in-part of Ser. No. 08/148,889, filed Nov. 8, 1993, abandoned and a continuation-in-part of Ser. No. 08/148,491, filed Nov. 8, 1993, abandoned.

BACKGROUND OF THE INVENTION

1. Field of the Invention

The present invention relates to glyoxylation-stabilized, arginine-containing synthetic lytic peptide compositions with enhanced resistance to proteolytic digestion, and to methods of making the same.

2. Description of Related Art

Naturally occurring amphipathic lytic peptides play an important if not critical role as immunological agents in insects and have some, albeit secondary, defense functions in a range of other animals. The function of these peptides is to destroy prokaryotic and other non-host cells by disrupting the cell membrane and promoting cell lysis. Common features of these naturally occurring amphipathic, lytic peptides include an overall basic charge, a small size (23–39 amino acid residues), and the ability to form amphipathic α-helices. Several types of amphipathic lytic peptides have been identified: cecropins (described in U.S. Pat. Nos. 4,355,104 and 4,520,016 to Hultmark et al.), defensins, sarcotoxins, melittin, and magainins (described in U.S. Pat. No. 4,810,777 to Zasloff). Each of these peptide types is distinguished by sequence and secondary structure characteristics.

Several hypotheses have been suggested for the mechanism of action of the lytic peptides: disruption of the membrane lipid bilayer by the amphipathic α-helix portion of the lytic peptide; lytic peptide formation of ion channels, which results in osmotically induced cytolysis; lytic peptide promotion of protein aggregation, which results in ion channel formation; and lytic peptide-induced release of phospholipids. Whatever the mechanism of lytic peptide-induced membrane damage, an ordered secondary conformation such as an α-amphipathic helix and positive charge density are features that appear to participate in the function of the lytic peptides.

Active analogs of naturally occurring lytic peptides have been produced and tested in vitro against a variety of prokaryotic and eukaryotic cell types (see for example Arrowood, M. J., et al. J. Protozool. 38: 161s [1991]; Jaynes, J. M., et al. FASEB J. 2: 2878 [1988]), including: gram positive and gram negative bacteria, fungi, yeast, envelope viruses, virus-infected eukaryotic cells, and neoplastic or transformed mammalian cells. The results from these studies indicate that many of the synthetic lytic peptide analogs have similar or higher levels of lytic activity for many different types of cells, compared to the naturally occurring forms. In addition, the peptide concentration required to lyse microbial pathogens such as-protozoans, yeast, and bacteria does not lyse normal mammalian cells.

The specificity of the lytic action depends upon the sequence and structure of the peptide, the concentration of the peptide, and the type of membrane with which it interacts. Jaynes et aL Peptide Research 2: 157 (1989) discuss the altered cytoskeletal characteristics of transformed or neoplastic mammalian cells that make them susceptible to lysis by the peptides. In these experiments, normal, human non-transformed cells remained unaffected at a given peptide concentration while transformed cells were lysed; however, when normal cells were treated with the cytoskeletal inhibitors cytochalasin D or colchicine, sensitivity to lysis increased. The experiments show that the action of lytic peptides on normal mammalian cells is limited. This resistance to lysis was most probably due to the well-developed cytoskeletal network of normal cells. In contrast, transformed cell lines which have well-known cytoskeletal deficiencies were sensitive to lysis. Because of differences in cellular sensitivity to lysis, amphipathic peptide concentration can be manipulated to effect lysis of one cell type but not another at the same locus.

Synthetic lytic peptide analogs can also act as agents of eukaryotic cell proliferation. Peptides that promote lysis of transformed cells will, at lower concentrations. promote cell proliferation in some cell types. This stimulatory activity is thought to depend on the channel-forming capability of the peptides, which somehow stimulates nutrient uptake, calcium influx or metabolite release, thereby stimulating cell proliferation (see Jaynes, J. M. Drug News & Perspectives 3: 69 [1990]; and Reed, W. A. et al. Molecular Reproduction and Development 31: 106 [1992]). Thus, at a given concentration, these peptides stimulate or create channels that can be beneficial to the normal mammalian cell in a benign environment where it is not important to exclude toxic compounds.

The synthetic lytic peptide analogs typically contain as few as 12 and as many as 40 amino acid residues. A phenylalanine residue is often positioned at the amino terminus of the protein to provide an aromatic moiety analogous to the tryptophan residue located near the amino terminus of natural cecropins and a UV-absorbing moiety with which to monitor the purification of the synthetic peptide. The basis for the design of these lytic peptide analogs is that an amphipathic peptide of minimal length and containing overall positive charge density effects lytic activity. Peptides that have the structural motif of a β-pleated sheet and overall positive charge density can also effect lytic activity.

As discussed in the preceding paragraph, in vitro laboratory tests of the lytic peptide analogs have been successful. However, the use of the lytic peptide analogs in vivo could be considerably limited in circumstances where proteases may digest the peptide analogs before sufficient pathogen cell lysis has occurred. In particular, the high concentration of positively charged amino acids such as lysine and arginine make the synthetic peptides susceptible to tryptic digestion. The secondary conformation of the peptides sequesters the hydrophobic amino acid residues, thus shielding them from interaction with proteases such as chymotrypsin, which hydrolyzes peptides at bulky or aromatic amino acid residues. This proteolytic susceptibility is a general problem for peptides and proteins when used in vivo. Many techniques are suitable for stabilizing proteins for in vitro use but are not appropriate for in vivo or oral administration to humans and animals.

Several studies teach that chemical modification of arginine residues has been used to study structure-function relationships in a variety of naturally occurring proteins and their substrates. For example, Busby et al., Arch. Biochem. Biophys 177: 552 (1976) teach that chemical modification of arginine residues with 1,2-cyclohexanedione can be used to study the essential nature of arginine residues in the maintenance of biological activity. This report states that the arginine residues in the test protein, plasma α-1 anti-trypsin, do not participate in the catalytic reaction.

Lin et al., Biochim. et Biophys. Acta 1159: 255 (1992) teach that α-bungarotoxin, a long-chain neurotoxin containing three arginine residues, can be derivatized on the arginine residues using either 1,2-cyclohexanedione or p-hydroxylphenylglyoxal. The effect of arginine modification on biological activity was tested by examining the binding activity of the modified toxin to the nicotinic acetylcholine receptor. None of the modified arginine residues were essential for binding to the receptor, however, the modification resulted in diminution of lethality and binding affinity. Thus, the article relates only to binding characteristics and biological activity of a modified neurotoxin and does not address enhanced proteolytic resistance of the protein.

Patthy et al., J. Biol. Chem. 250: 557 (1975) and J. Biol. Chem. 250: 565 (1975) teach that modification of arginine residues in lysozyme using 2,3-butanedione, phenylglyoxal or glyoxal showed that lysozyme retained biological activity.

Accordingly, it would be a significant advance in the art to provide a method of producing chemically modified physiologically active lytic peptides that have enhanced resistance to proteolysis.

It would be particularly desirable to provide a method of producing such peptides so that the modified peptides have enhanced proteolytic stability and retain their physiological activity for in viva applications against pathogenic microbial organisms such as bacteria, yeast, fungi, and protozoans; neoplastic or transformed cells; envelope viruses; and virally-infected cells.

These and other objects and advantages will be more fully apparent from the ensuing disclosure and claims.

SUMMARY OF THE INVENTION

The present invention relates generally to glyoxylation-stabilized, arginine-containing synthetic lytic peptide compositions, and to methods of making the same.

More specifically, the present invention relates in a broad compositional aspect to chemically modified, arginine-containing synthetic peptides, wherein the side chain of the arginine residues are glyoxylated.

In one particular aspect, the present invention relates to a physiologically active peptide composition comprising a synthetic physiologically active peptide that has been chemically modified, wherein the side chain of the arginine residues are glyoxylated such that the chemically modified physiologically active peptide has enhanced in vivo resistance to enzymatic digestion, relative to the physiologically active peptide alone.

The invention relates in a further aspect to a physiologically active peptide composition comprising a physiologically active synthetic peptide that has been chemically modified, wherein the ε-amino group of the lysine residue and the α-amino group of the N-terminal amino acid have been first been methylated, and the side chain of the arginine residues are subsequently glyoxylated such that the chemically modified physiologically active peptide has enhanced in vivo resistance to proteolytic digestion, relative to the physiologically active peptide alone.

In another aspect, the present invention relates to a group of similar physiologically active peptide compositions, comprising: (i) physiologically active synthetic peptides that have been chemically modified, wherein the side chain of the arginine residues are glyoxylated; and (ii) chemically modified, physiologically active synthetic peptides that are related by amino acid sequence and physiological activity.

In another aspect, the invention relates to a physiologically active peptide composition comprising synthetic peptides which contain as few as 12 and as many as 40 amino acid residues, wherein the peptide is composed mainly of the following amino acid residues: alanine, aspartate, arginine, glycine, isoleucine, leucine, lysine, and valine. A phenylalanine residue is present near the N- or C-terminus of the peptide.

The invention relates in a further aspect to a physiologically active peptide composition comprising a physiologically active synthetic peptide that has been chemically modified, wherein the guanido group of the arginine residues are glyoxylated. In such a peptide, the secondary conformation of the peptide is an amphipathic α-helix, in which one side of the cylinder is hydrophilic, with the polar amino acid residues projecting into the aqueous medium. The other side of the cylinder is hydrophobic, with the hydrophobic amino acid residues seeking an anhydrous environment.

The invention relates in a further aspect to a physiologically active peptide composition comprising a physiologically active synthetic peptide that has been chemically modified, wherein the guanido groups of arginine residues and the N-terminal α-amino group are glyoxylated. In such a peptide, the secondary conformation of the peptide is in a periodic structural motif, the β-pleated sheet, in which the polypeptide chain is extended in a sheet-like conformation rather than a cylinder-like conformation.

The invention relates in yet a further aspect to a physiologically active peptide composition comprising a physiologically active synthetic peptide that has been chemically modified, wherein the guanido groups of the arginine residues are glyoxylated. In such a peptide, the secondary conformation is an amphipathic α-helix. With such a conformation in an aqueous environment, the hydrophobic regions would adhere to each other to form micelles and hence isolated domains of a separate phase. The dimethylated lysine side chain residues and the glyoxylated arginine residues that have enhanced resistance to tryptic hydrolysis are exposed to the aqueous environment, and hence to proteolytic enzymes.

The invention relates in yet a further aspect to a physiologically active peptide composition comprising a physiologically active synthetic peptide that has been chemically modified, wherein the guanido groups of arginine residues and the N-terminal α-amino group are glyoxylated. In such a peptide, the secondary conformation of the peptide is in a periodic structural motif, the β-pleated sheet. In such a configuration, individual polypeptides can associate into overlapping structures. This association is stabilized by hydrogen bond formation between NH and CO groups in separate polypeptide strands The invention relates in a further aspect to a physiologically active peptide composition comprising a physiologically active synthetic peptide that has been chemically modified, wherein the guanido groups of arginine residues and the N-terminal α-amino group are glyoxylated. Such a peptide is used in vivo to treat infections caused by pathogenic microbial organisms such as bacteria, yeast, fungi, and protozoans by lysing these organisms; to treat cancers caused by neoplastic or transformed cells by lysing such cells; and to treat viral infections by lysing envelope viruses and virally-infected cells.

The term "amphipathic" as used herein refers to the distribution of hydrophobic and hydrophilic amino acid residues along opposing faces of an α-helix structure or other secondary conformation, which results in one face of the a-helix structure being predominantly hydrophobic and the other face being predominantly hydrophilic. The degree of amphipathy of a peptide can be assessed by plotting the sequential amino acid residues on an Edmunson helical wheel.

The term "peptide" as used herein is intended to be broadly construed as inclusive of polypeptides per se having molecular weights of up to 10,000 daltons, as well as proteins having molecular weights of greater that about 10,000 daltons, wherein the molecular weights are number average molecular weights.

The term "methylated" as used herein means that the specified amino groups have been chemically reacted by a method of reductive alkylation or methylation so that the associated hydrogen atoms are replaced by covalently coupled methyl groups.

The term "glyoxylated" as used herein means that the specified guanido and α-amino groups have been chemically reacted such that each is covalently coupled to a glyoxal group.

DETAILED DESCRIPTION OF THE INVENTION AND PREFERRED EMBODIMENTS THEREOF

Chemical modification of lytic peptide analogs offers certain advantages. If the modifications are made in such a way that the lytic peptides retain all or most of their biological activity, then the following advantage results: the peptides have enhanced stability to proteolysis. With enhanced stability, the peptides can be administered in vivo without loss of biological activity through proteolytic digestion.

When considering lytic peptide analog stabilization with chemical modification of amino acid residue side chains, it is important to consider the character (hydrophobic or hydrophilic) and location of the individual amino acids residues within the peptides of concern. With the lytic peptide analogs proposed herein, the following are the only types of amino acid residues to be examined: phenyalanine, alanine, aspartate, valine, isoleucine, leucine, glycine, lysine, and arginine. Of this group, lysine, arginine and aspartate are potentially exposed to proteases in the aqueous environment, as a result of the secondary conformation of the peptide. In peptides containing aspartate. this group could be previously chemically modified to mask the amino acid residue. The ε-amino groups of the lysine residues would be also previously methylated to mask the lysine side chains.

The lytic peptide analogs are designed to take the configuration of an amphipathic α-helix structure or a β-pleated sheet conformation. In an aqueous environment the hydrophobic regions of these peptides would adhere to each other, forming micelles and hence isolated domains of a separate phase. In this circumstance, the hydrophobic moieties would be unavailable to the aqueous phase and hence to hydrolysis by proteolytic enzymes. In one preferred aspect of the invention, the lytic peptides assume the secondary conformation of an amphipathic α-helix.

Each arginine side chain contains a side chain guanido group which provides the peptide, at physiological pH with a unit positive charge. The combined multiple charge of each arginine guanido group contributes to the polarity and thus the regional hydrophilicity required for formation of an amphipathic α-helix. The positive charge of these lytic peptide analogs is required for activity. Amphipathy alone does not provide for lytic action. Modification of the side chain group of the arginine amino acid residue does not affect the unit charge of the arginine residue or the peptide. However, susceptibility to tryptic hydrolysis for the arginine residue α-carbonyl peptide linkages is drastically reduced.

As discussed above, it can be presumed that alanine, valine, leucine, isoleucine, glycine, internal phenylalanine, aspartate, and lysine residues contained in the lytic peptide analogs are not vulnerable to proteolytic attack due to their removal from the aqueous phase or prior chemical masking. Arginine. however, provides a specific locus for the most aggressive proteolytic enzyme, trypsin. For this reason, glyoxylation of the lytic peptides would provide enhanced stability to proteolytic hydrolysis. It should also be noted that the N-terminal α-amino group is also exposed and would also become glyoxylated during such a procedure unless the peptide was subjected to prior methylation, thus providing further resistance to both chymotrypsin, which attacks aromatic amino acids such as phenylalanine, and aminopeptidases, which act at the N-terminus.

One objective of the present invention is to provide enhanced proteolytic stability to a series of arginine-containing, lytic peptide analogs. Another objective is to use such modified lytic peptides for in vivo delivery of physiologically effective lytic peptides.

The features and advantages of the invention are more fully shown by the following illustrative examples and embodiments, which are not to be limitingly construed as regards the broad scope, utility, and applicability of the invention.

EXAMPLE 1

Representative Lytic Peptides

Set out in Table 1 below as illustrative examples of amphipathic peptide analogs of the present invention are the amino acid sequences of a family of related peptide analogs. The peptides may be synthesized according to conventional methods using a Milligen™ phase peptide synthesizer. Representative peptides from this group are methylated, oxylated, and used in subsequent experimental examples. The three letter amino acid symbols are as follows: Ala, alanine; Arg, arginine; Asp, aspartate; Gly, glycine; Ile, isoleucine; Leu, leucine; Lys, lysine; Phe, phenylalanine; and Val, valine. These amphipathic peptide analogs are designated for ease of reference as SEQ ID NO. 7–14.

TABLE 1

PEPTIDE SEQUENCES

SEQ ID NO: 7 Phe Ala Val Gly Leu Arg Ala Ile Lys Arg Ala Leu Lys Lys Leu Arg
              1           5               10              15

TABLE 1-continued

PEPTIDE SEQUENCES

```
            Arg Gly Val Arg Lys Val Ala Lys Arg Lys Arg
                         20              25

SEQ ID NO: 8  Phe Ala Val Gly Leu Arg Ala Ile Lys Arg Ala Leu Lys Lys Leu Arg
              1               5                   10                  15
              Arg Gly Val Arg Lys Val Ala
                           20

SEQ ID NO: 9  Lys Arg Lys Arg Ala Val Lys Arg Val Gly Arg Arg Leu Lys Lys Leu
              1               5                   10                  15
              Ala Arg Lys Ile Ala Arg Leu Gly Val Ala Phe
                           20                  25

SEQ ID NO: 10 Ala Val Lys Arg Val Gly Arg Arg Leu Lys Lys Leu Ala Arg Lys Ile
              1               5                   10                  15
              Ala Arg Leu Gly Val Ala Phe
                           20

SEQ ID NO: 11 Phe Ala Val Gly Leu Arg Ala Ile Lys Arg Ala Leu Lys Lys Leu Arg
              1               5                   10                  15
              Arg Gly Val Arg Lys Val Ala Lys Arg Lys Arg Lys Asp Leu
                           20                  25                  30

SEQ ID NO: 12 Phe Ala Val Gly Leu Arg Ala Ile Lys Arg Ala Leu Lys Lys Leu Arg
              1               5                   10                  15
              Arg Gly Val Arg Lys Val Ala Lys Asp Leu
                           20                  25

SEQ ID NO: 13 Lys Arg Lys Arg Ala Val Lys Arg Val Gly Arg Arg Leu Lys Lys
              1               5                   10              15
              Leu Ala Arg Lys Ile Ala Arg Leu Gly Val Ala Phe Lys Asp Leu
                           20                  25                  30

SEQ ID NO: 14 Ala Val Lys Arg Val Gly Arg Arg Leu Lys Lys Leu Ala Arg Lys Ile
              1               5                   10                  15
              Ala Arg Leu Gly Val Ala Phe Lys Asp Leu
                           20                  25
```

Chemicals modification of lytic peptide analogs offers certain advantages. If the modifications are made in such a way that the peptides retain all or most of their lytic characteristics, then physiologically active peptides have enhanced stability to proteolyisis. With enhanced stability, oral delivery of the peptide is advantageously accomodated without excessive loss of activity due to proteolytic digestion.

EXAMPLE 2

Chemical Modification by Glyoxylation

An exemplary and preferred reaction scheme for glyoxylation of the guanido groups of arginine residues and the N-terminal α-amino acid in a representative lytic peptide is describe below.

Potential reagents which are capable of modifying the guanido group arginine under mild conditions and do not require an additional reduction reaction are 2,3-butanedione, phenylglyoxal, and glyoxal. The adducts from 2,3-butanedione and phenylglyoxal were judged to be too unstable, and glyoxal was therefore chosen as the preferred derivatizing reagent. The chemical reaction scheme is described below.

REACTION SCHEME: GLYOXYLATION OF PEPTIDYL ARGININE

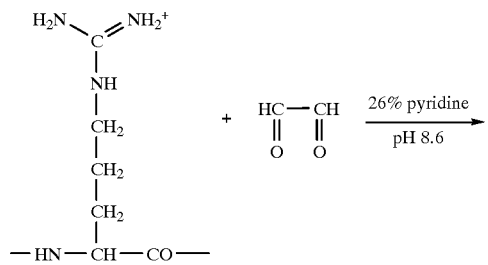

-continued

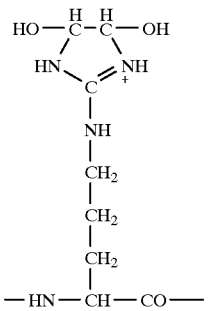

In the glyoxylation reaction, an arginine-containing peptide, Shiva 10R (a cecropin analog) was used as a convenient test substrate. The sequence of the 23-mer test peptide is: Phe-Ala-Arg-Arg-Leu-Ala-Arg-Arg-Leu-Arg-Arg-Leu-Ala-Arg-Arg-Leu-Ala-Arg-Leu-Ala-Leu-Ala-Leu. The peptide (5 mg) was dissolved in 1.0 ml of 80% pyridine to form a clear solution. To this mixture 2 ml of 0.5 M sodium bicarbonate buffer pH 8.0 ($NaHCO_3$-NaOH) was added. Freshly prepared, 30% glyoxal suspension in the 0.5 M sodium bicarbonate buffer was added to the reaction volume and the cloudy reaction mixture was stirred at room temperature for three hours. This concentration of glyoxal is convenient for the reaction, however, the concentration of glyoxal can be varied according to the needs of the reaction. After 20 minutes the solution became mostly clear although progressively yellow-brown during the course of the reaction. The final concentration of the pyridine was 23%, a convenient concentration for the purposes of this reaction. The concentration of pyridine can be varied according to the needs of the reaction. The pyridine, as a representative heterocyclic amine, was essential to the reaction, in order to maintain the glyoxal/peptide mixture in solution. Other hetrocyclic amines or water-soluble dielectric solvents such as the heterocyclic amine piperidine were tested and can be used in the place of pyridine.

At the conclusion of the reaction, glacial acetic a&id was added drop-wise to bring the pH to 6.0. A two-phase extraction using three parts ether to one part acetone for the organic phase was repeated three times to remove the majority of the glyoxal. The pyridine was not removed to a significant extent. The preparation was dried in a lyophilizer and the crusty residue was rinsed with three parts ether to one part acetone. The residual ether-acetone was removed in vacuo. The cloudy ether-acetone supernatant was centrifuged to recover a precipitate which was pooled with the remaining residue by washing the tube with glacial acetic acid. The residue was dissolved in glacial acetic acid and a small amount of insoluble material was removed by centrifugation. The solution was then applied to a G-15-120 Sephadex® column (2.4×31 cm) and eluted with 0.1 M acetic acid. The recovered fraction were lyophilized to dryness overnight.

The peptide was stored at −20° C. in the presence of a desiccant as their acetate salt. For use in the following examples modified peptides were dissolved in a saline buffer, pH 7.0 at a concentration of 0.1 mg/ml to 10 mg/ml.

EXAMPLE 3

Determination of Arginyl Glyoxylation and Trygtic Resistance

A spectrophotometric assay of the unsubstituted amino groups was used to determine the susceptibility of the glyoxylated peptide from example 2 to tryptic digestion. Since arginine incorporated into a peptide does not provide a free amino group for monitoring, the amino groups liberated on tryptic hydrolysis would provide evidence of resistance or susceptibility to tryptic action. The procedure uses 2,4,6-trinitrobenzenesulfonic acid (TNBS, picrylsulfonic acid) which produces a visible yellow color and a UV absorbance maximum at 335 nm when esterified to unsubstituted amino groups (Habeeb, A.S.F.A., Anal. Biochem. 14: 328 [1966]).

The procedure is described as follows. The tryptic digestion reaction was performed first, then the TNBS spectrophotometric assay. The buffer for tryptic digestion contains 0.1 M KCl, 0.05 M $CaCl_2$, and 0.01 M TRIS-HCl, pH 7.75. 9600 units of immobilized trypsin on glass beads from Sigma is mixed in 5 ml of the digestion buffer (imm-trypsin). The representative peptide, either glyoxylated or unmodified, is at a concentration of 3 mg/ml. To each of the following 5 ml culture tubes, designated a-e, the following solutions were added:

TABLE 2

REACTION MIXTURES

| Sample | +/− Trypsin |
|---|---|
| a. 0.2 ml unmodified peptide + | 0.1 ml digestion buffer |
| b. 0.2 ml glyoxylated peptide + | 0.1 ml digestion buffer |
| c. 0.2 ml unmodified peptide + | 0.1 ml imm-trypsin |
| d. 0.2 ml glyoxylated peptide + | 0.1 ml imm-trypsin |
| e. 0.2 ml $H_2O$ (self digestion control) + | 0.1 ml imm-trypsin |

The tubes were gently shaken for 30 minutes at room temperature.

At the conclusion of the trypsin digestion reaction, the TNBS spectrophotometric assay was performed on the samples. From the completed trypsin digestion reaction, 0.01 ml of each sample was placed in 5 ml assay tubes. Added to the assay tubes is 1.0 ml of 4% $NaHCO_3$, pH 8.5, 0.9 ml of $H_2O$ and 1.0 ml of TNBS. The reactions are incubated at 40° C. for 45–60 minutes. After the incubation period, 0.5 ml of 1N HCl is added to the tubes. If necessary, 1 ml of 10% sodium dodecyl sulfate may be added prior to the addition of the acid to prevent precipitation of the peptides. The absorbance at 335 nm is read versus a blank of the reagents minus peptide. The results are shown in the Table 3 below

TABLE 3

TRYPTIC DIGESTION RESISTANCE OF

GLYOXYLATED PEPTIDES

| Sample | Result |
|---|---|
| a. unmodified peptide | light yellow |
| b. glyoxylated peptide | clear |
| c. unmodified peptide + trypsin | strong yellow |
| d. glyoxylated peptide + trypsin | clear |
| e. H$_2$O + trypsin (self digestion control) | clear |

In this assay, an unmodified peptide would have only the N-terminal α-amino group available for reaction with TNBS, since the arginine side chains provide no free amino groups. A glyoxylated peptide would not have a free N-terminal α-amino group. Peptides hydrolyzed with trypsin would have free α-amino groups for each arginine residue that has been attacked by hydrolysis. The modified peptide from example 2 has nine arginine residues. The data from Table 3 can be interpreted as follows:

TABLE 4

RESULTS

| Peptide Sample | Possible # of free NH$_2$ | TNBS-reacted NH$_2$ |
|---|---|---|
| a. unmodified | 1 (N-terminal α-amino group) | 1 |
| b. glyoxylated | 0 | 0 |
| c. unmodified + trypsin | 10 (9 arginyl residues + 1 N-terminal) | 10 |
| d. glyoxylated + trypsin | 0 | 0 |
| e. H$_2$O + trypsin | unknown | 0 |

The information in Tables 2–4 demonstrate that the glyoxylated peptide was fully protected from hydrolysis by trypsin, whereas the unmodified peptide was susceptible to hydrolysis.

EXAMPLE 4

In Vitro Lysis of Pathogenic Bacteria

The effect of two lytic peptides, SEQ ID NO. 14 and DP-1 (a mellitin analog) were tested against pathogenic bacteria in vitro. DP-1 is a convenient test 23-mer lytic peptide with the sequence Phe-Ala-Leu-Ala-Leu-Lys-Ala-Leu-Lys-Lys-Ala-Leu-Lys-Lys-Leu-Lys-Lys-Ala-Leu-Lys-Lys-Ala-Leu. In this test, antibiotic resistant clinical isolates of *Pseudomonas aeruginosa* and *Staphylococcus aureus* were obtained. The lytic peptide bioassay was performed as described below.

A flask containing 49 ml of nutrient broth was inoculated with 1 ml of an overnight culture of the test bacteria. The culture was allowed to grow to mid-log phase at 37° C. with shaking (approximately 4 hours). When the cells reached the correct density, the cells were transferred to a sterile tube and centrifuged for 10 minutes at 3000 rpm. The pellet was resuspended in 3 ml of phosphate buffer and centrifuged for 10 minutes at 3000 rpm. The pellet was resuspended once again in sufficient (but measured) volume to calculate the absorbance of the suspension at 600 nm. Using the resulting absorbance and a previously constructed growth curve, the required dilution to achieve a concentration of 10$_6$ cells/ml was determined.

One micromole of the test peptide was dissolved in 1.0 ml of 0.01% acetic acid to make a 1 mM solution and serial dilutions were made to give a range of peptide concentrations from 10 μM to 1 mM. The test culture tubes for the bioassay contained 800 μl of phosphate buffer, pH 7.0, 100 μl of cells at 10$_6$ cells/ml and 100 pl of peptide solution (10 μM to 1 mM). The final concentration of peptide in the assay was from 1 μM to 100 μM. A reaction system minus peptide was included as a control. The tubes were incubated at 37° C. for one hour.

After the incubation period, two 1:10 serial dilutions in phosphate buffer were made for each culture (three 1:10 serial dilutions for the control culture). 100 μl of each dilution was spread on a nutrient agar plate, in duplicate and incubated overnight at 37° C. The following day, the number of colonies on the control plates was counted to determine the starting number of cells in the assay tubes. The number of cells surviving the assay in the presence of peptide was also counted. The results are shown in Table 5.

TABLE 5

BACTERICIDAL ACTIVITY OF MODIFIED AND UNMODIFIED PEPTIDES WITH A CLINICAL ISOLATE OF *PSEUDOMONAS AERUGINOSA*

| Peptide | μM | Modification[a] | # of Survivors | % of Control |
|---|---|---|---|---|
| minus peptide | 0 | | 100,000 | 100 |
| SEQ ID NO. 14 | 10 | | 2 | 0.002 |
| SEQ ID NO. 14 | 10 | m, g | 91 | 0.09 |
| SEQ ID NO. 14 | 1 | | 100,000 | 100 |
| SEQ ID NO. 14 | 1 | m, g | 100,000 | 100 |
| DP-1 | 10 | | 6,607 | 6.6 |
| DP-1 | 10 | m | 2,042 | 2 |
| DP-1 | 1 | | 100,000 | 100 |
| DP-1 | 1 | m | 100,000 | 100 |

[a]m = methylated lysine residues, g = glyoxylated arginine residues.

This data in this table shows that the modification of the peptides does not affect their bacteriolytic activity. Each peptide has a different extent of bacteriolytic activity for a given bacterial species aat a given concentratrion. In general, the pepteides in this experiment demostrated bacteriolytic acitvity at a concentration of 10 μM, but not at a concentrartion of 1 μM.

TABLE 6

BACTERICIDAL ACTIVITY OF MODIFIED AND UNMODIFIED PEPTIDES WITH A CLINICAL ISOLATE OF *STAPHYLOCOCCUS AUREUS*

| Peptide | μM | Modification[a] | # of Survivors | % of Control |
|---|---|---|---|---|
| minus peptide | 0 | | 50,000 | 100 |
| SEQ ID NO. 14 | 10 | | 2,299 | 4.6 |
| SEQ ID NO. 14 | 10 | m, g | 2,818 | 5.6 |
| SEQ ID NO. 14 | 1 | | 50,000 | 100 |
| SEQ ID NO. 14 | 1 | m, g | 50,000 | 100 |
| DP-1 | 10 | | 813 | 1.6 |
| DP-1 | 10 | m | 891 | 1.8 |
| DP-1 | 1 | | 50,000 | 100 |
| DP-1 | 1 | m | 50,000 | 100 |

[a]m = methylated lysine residues, g = glyoxylated arginine residues.

This data in this table shows that the modification of the peptides does not affect their bacteriolytic activity. Each peptide has a different extent of bacteriolytic activity for a given bacterial species at a given concentration. In general, the peptides in this experiment demostrated activity at a concentration of 10 μM, but not a concentration of 1 μM.

While the invention has been described herein, with certain features, and embodiments it will be recognized that the invention may be widely varied, and that numerous other modifications, variations, and other embodiments are possible, and such modification, variations, and other embodiments are to be regarded as being within the spirit and scope of the invention.

What is claimed is:

1. A non-neurotoxin, arginine residue-containing lytic peptide of enhanced tryptic digestion resistance, comprising glyoxylated guanido groups on the arginine residues.

2. A peptide of claim 1 wherein the peptide is a non-naturally occurring α-helical amphipathic lytic peptide.

3. A peptide of claim 1 wherein the peptide is a non-naturally occurring β-pleated sheet lytic peptide.

4. A non-neurotoxin, arginine residue-containing peptide according to claim 1 whose sequence of amino acid residues comprises from 12 to 40 amino acid residues.

5. A non-neurotoxin, arginine residue-containing peptide according to claim 1 wherein the peptide is a non-naturally occurring lytic peptide wherein the ε-amino groups on the lysine residues and the α-amino group of the N-terminal amino acid residue are methylated.

6. A non-neurotoxin, arginine residue-containing peptide according to claim 1 whose sequence of amino acids also contains a phenylalanine residue at the N-terminus of the peptide.

7. A non-neurotoxin, arginine residue-containing peptide according to claim 1 wherein the peptide has an N-terminal phenylalanine residue, the α-amino group of which is sufficiently glyoxylated in order to enhance resistance of the peptide to chymotryptic digestion, in addition to tryptic digestion.

8. A non-neurotoxin, arginine residue-containing peptide according to claim 1 wherein the lytic peptide has the α-amino group of the N-terminal amino acid residue sufficiently glyoxylated in order to enhance resistance of the peptide to aminopeptidase digestion, in addition to tryptic digestion.

9. A non-neuroxin, arginine residue-containing peptide according to claim 1 whose sequence of amino acid residues is selected from the group consisting of:

```
SEQ ID NO:7    Phe Ala Val Gly Leu Arg Ala Ile Lys Arg Ala Leu Lys Lys Leu Arg
               1               5                   10                  15
               Arg Gly Val Arg Lys Val Ala Lys Arg Lys Arg
                           20                  25

SEQ ID NO:8    Phe Ala Val Gly Leu Arg Ala Ile Lys Arg Ala Leu Lys Lys Leu Arg
               1               5                   10                  15
               Arg Gly Val Arg Lys Val Ala
                           20

SEQ ID NO:9    Lys Arg Lys Arg Ala Val Lys Arg Val Gly Arg Arg Leu Lys Lys Leu
               1               5                   10                  15
               Ala Arg Lys Ile Ala Arg Leu Gly Val Ala Phe
                           20                  25

SEQ ID NO:10   Ala Val Lys Arg Val Gly Arg Arg Leu Lys Lys Leu Ala Arg Lys Ile
```

-continued

```
                   1              5              10             15
                  Ala Arg Leu Gly Val Ala Phe
                                  20

SEQ ID NO:11  Phe Ala Val Gly Leu Arg Ala Ile Lys Arg Ala Leu Lys Lys Leu Arg
                   1              5              10             15
                  Arg Gly Val Arg Lys Val Ala Lys Arg Lys Arg Lys Asp Leu
                                  20                  25                 30

SEQ ID NO:12  Phe Ala Val Gly Leu Arg Ala Ile Lys Arg Ala Leu Lys Lys Leu Arg
                   1              5              10             15
                  Arg Gly Val Arg Lys Val Ala Lys Asp Leu
                                  20                  25

SEQ ID NO:13  Lys Arg Lys Arg Ala Val Lys Arg Val Gly Arg Arg Leu Lys Lys
                   1              5              10             15
                  Leu Ala Arg Lys Ile Ala Arg Leu Gly Val Ala Phe Lys Asp Leu
                                  20                  25                 30

SEQ ID NO:14  Ala Val Lys Arg Val Gly Arg Arg Leu Lys Lys Leu Ala Arg Lys Ile
                   1              5              10             15
                  Ala Arg Leu Gly Val Ala Phe Lys Asp Leu
                                  20                  25
```

10. A method of treating a disease state selected from the group consisting of:

neoplasias, viral infections, bacterial infections, protozoan infections, fungal infections, and yeast infections, comprising administering to a subject having or susceptible to said disease state a non-neurotoxin, arginine residue-containing peptide of enhanced tryptic digestion resistance, comprising glyoxylated guanido groups on the arginine residues and glyoxylated α-amino groups at the N-terminus of the peptide.

* * * * *